United States Patent
Luo et al.

(10) Patent No.: US 11,743,715 B2
(45) Date of Patent: Aug. 29, 2023

(54) DEVICES, SYSTEMS AND METHODS FOR CLOSE CONTACT TRACING WITH STRONG PRIVACY PROTECTION

(71) Applicant: Cypress Semiconductor Corporation, San Jose, CA (US)

(72) Inventors: Hui Luo, Marlboro, NJ (US); Kamesh Medapalli, San Jose, CA (US)

(73) Assignee: Cypress Semiconductor Corporation, San Jose, CA (US)

( * ) Notice: Subject to any disclaimer, the term of this patent is extended or adjusted under 35 U.S.C. 154(b) by 107 days.

(21) Appl. No.: 17/217,775

(22) Filed: Mar. 30, 2021

(65) Prior Publication Data
US 2022/0104008 A1    Mar. 31, 2022

Related U.S. Application Data

(60) Provisional application No. 63/084,431, filed on Sep. 28, 2020.

(51) Int. Cl.
| | | |
|---|---|---|
| G06F 7/04 | (2006.01) | |
| H04N 7/16 | (2011.01) | |
| H04W 12/02 | (2009.01) | |
| H04W 12/06 | (2021.01) | |
| H04W 12/04 | (2021.01) | |
| H04W 12/61 | (2021.01) | |
| H04L 9/30 | (2006.01) | |
| H04W 4/80 | (2018.01) | |
| H04W 76/10 | (2018.01) | |
| H04W 4/029 | (2018.01) | |
| G01S 1/04 | (2006.01) | |
| H04W 12/033 | (2021.01) | |

(Continued)

(52) U.S. Cl.
CPC .......... *H04W 12/02* (2013.01); *G01S 1/0428* (2019.08); *H04L 9/30* (2013.01); *H04W 4/029* (2018.02); *H04W 4/80* (2018.02); *H04W 12/033* (2021.01); *H04W 12/04* (2013.01); *H04W 12/06* (2013.01); *H04W 12/61* (2021.01); *H04W 76/10* (2018.02); *G06Q 30/0251* (2013.01); *G06Q 50/265* (2013.01); *G16H 40/20* (2018.01); *G16H 50/80* (2018.01); *H04L 2209/80* (2013.01)

(58) Field of Classification Search
CPC ... H04W 12/02; H04W 12/033; H04W 12/06; H04W 12/04; H04W 12/61; H04W 4/80; H04W 4/029; H04L 9/30
USPC .......................................................... 726/26
See application file for complete search history.

(56) References Cited

U.S. PATENT DOCUMENTS

| | | | |
|---|---|---|---|
| 10,219,106 B1 * | 2/2019 | Lam ................... | H04W 12/108 |
| 2017/0164142 A1 * | 6/2017 | Rykowski ............ | H04W 12/06 |

(Continued)

*Primary Examiner* — Jeffrey C Pwu
*Assistant Examiner* — Samuel U Ambaye

(57) ABSTRACT

A method can include, by operation of a user device, receiving beacon data via a wireless signal. Beacon data can include unencrypted data that includes a key identification (ID) corresponding to a private key/public key pair, a time value, and a location value. Beacon data can also include encrypted data that includes at least a beacon ID, a beacon time value, and a beacon location value. If the unencrypted time value is within a predetermined range of a current time value of the user device, the beacon data can be stored in a user record with a user ID. Periodically, the user record can be uploaded to a tracking system. Corresponding devices and systems are also disclosed.

17 Claims, 18 Drawing Sheets

(51) Int. Cl.
  *G16H 40/20* (2018.01)
  *G16H 50/80* (2018.01)
  *G06Q 50/26* (2012.01)
  *G06Q 30/0251* (2023.01)

(56) References Cited

U.S. PATENT DOCUMENTS

2022/0046023 A1* 2/2022 Friend .................. H04L 63/107
2022/0200789 A1* 6/2022 Lalande ................ H04W 12/50

* cited by examiner

BEACON DEVICE

DEVICES, SYSTEMS AND METHODS FOR CLOSE CONTACT TRACING WITH STRONG PRIVACY PROTECTION

This application claims the benefit of U.S. provisional patent application having Ser. No. 63/084,431, filed on Sep. 28, 2020, the contents of which are incorporated by reference herein.

TECHNICAL FIELD

The present disclosure relates generally to contact tracking systems, and more particularly to contact tracking system that preserve the privacy of users.

BACKGROUND

Current solutions for tracking people's close contact history, such as for determining exposure to contagious diseases, can raise many privacy concerns. Some governments track people using security camera footage, global position system (GPS) data from cell phones, and credit card transactions. Such methods provide little, if any privacy for the parties involved. Other countries, including many European countries and the United States have used the Google/Apple Exposure Notification (GAEN) system, which can provide for better privacy.

Conventional contact tracing systems, like GAEN, can include an application (app) running on a user's mobile phone. The app can generate Rolling Proximity Identifiers (RPIs) derived from a random Daily Tracking Key (DTK) and a time value. The RPI can be updated every 10-15 minutes. The app can periodically broadcast its RPI according to the Bluetooth Low Energy (BLE) standard. The app also stores all observed RPIs from other phones as close contact evidence.

If someone is infected, they notify a GAEN server and sending all recent DTKs to the server. All apps will periodically pull all recent DTKs of reported infected users from the server and derive all RPIs from the DTKs. Once an app finds it observed a RPI from an infected person, it notifies the user.

Conventional systems, like GAEN, can still present some privacy concerns. In such systems an RPI can be constant before it is updated at a specified time interval, and so can be used to track the user by observers in close proximity to the user. Further, after an infected user notifies the server, his/her recent DTKs are broadcast by the server. Observers in close proximity can identify the user by calculating the user's RPI with the DTK of that day (and any day after the user remains affected but still go out). In addition, conventional approaches can suffer from high inquiry data volume if DTKs are frequently updated. However, infrequently updated DTKs can potentially reveal identities of reported users, as noted above. Also, infrequent RPI broadcast can result in missed detections in cases where two people go to the same spot at slightly different times, so their phones cannot observe each other's RPIs.

Conventional systems that utilize Bluetooth technology can suffer from accuracy problems in determining close proximity.

It would be desirable to arrive at a contact tracing system that does not suffer from the drawbacks noted above.

DETAILED DESCRIPTION

Figure 1:
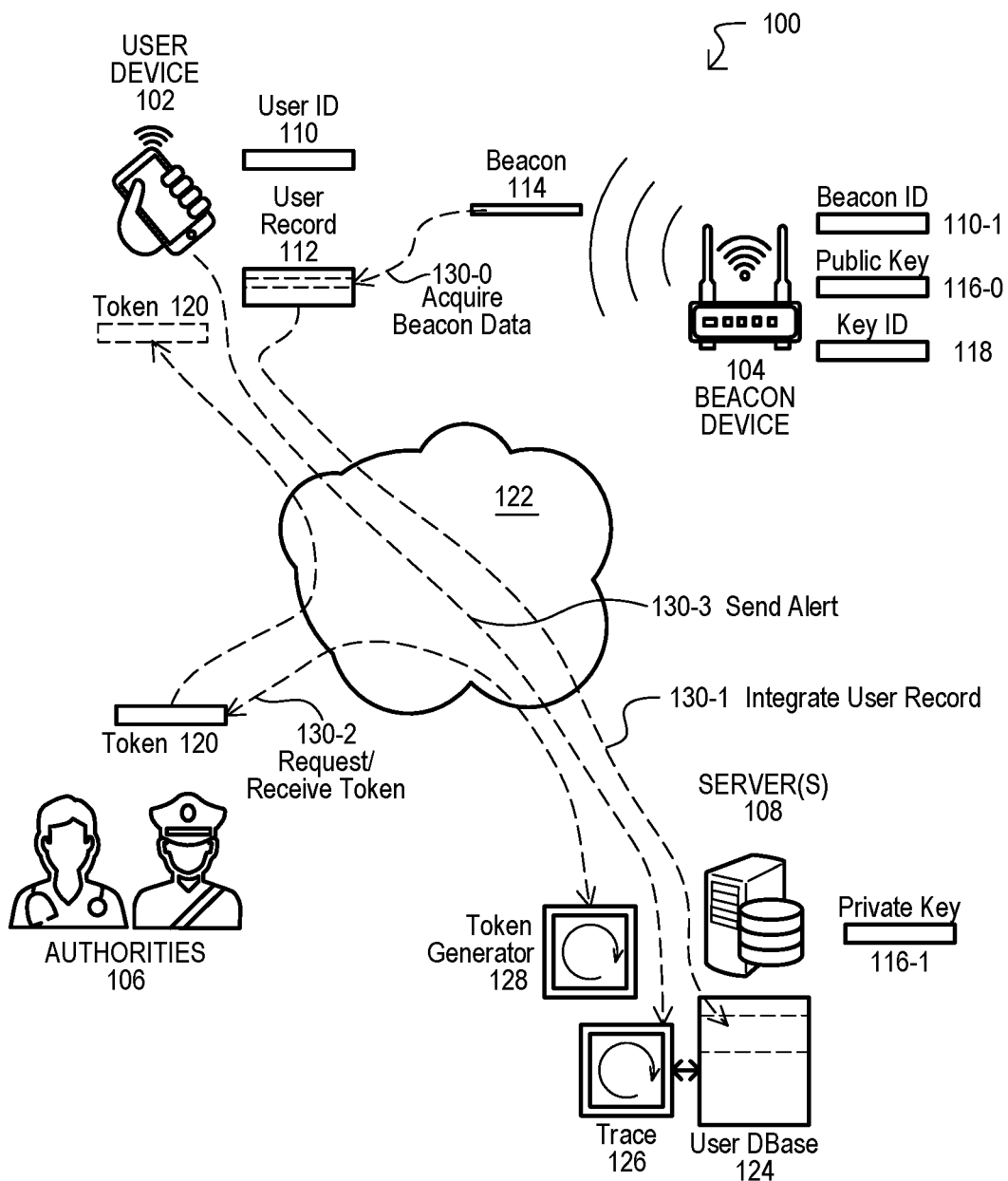
FIG. 1 is a diagram of a close contact tracking system according to an embodiment.

Embodiments herein are directed to devices, methods and systems that can track a close contact history of users and send alert information to relevant users without revealing any users' identity.

According to embodiments, a system can include beacon devices, user devices, and a tracking system. User devices can anonymously register with the tracking system. Beacon devices can wirelessly issue beacons that include data encrypted with a public key and a key ID that identifies the public key. User devices can receive and store beacon data, and periodically transmit it to the server system with a user ID. Based on key ID values, the tracking system can use corresponding private keys to decrypt and verify beacon data, and then incorporate the beacon data into a searchable database.

In an alert event, a user can contact an authority that has been authenticated with the tracking system. The authority can request a time-limited token from the tracking system, and blindly forward it to the user. The user can submit an alert to the tracking system with the token and a user ID. Upon verifying the validity of the token, the tracking system can search the database and issue alerts to other users determined to have been in close contact with the alerting user.

User devices can also function as beacon devices, periodically transmitting their own beacons. Similarly, beacon devices can function as user devices, accumulating beacon data from other devices and transmitting the beacon data to the tracking system.

In some embodiments, upon receiving a beacon, a user device can determine a distance from the beacon device, and include the distance data when sending its accumulated beacon data to the tracking server.

In some embodiments, beacon data can include a key ID, an unencrypted time value, a location value, and the same time and location value encrypted using the tracking system's public key identified by the key ID. User devices can discard beacon data having an unencrypted time (and/or location) value that sufficiently varies from the user devices own time (and/or location).

According to embodiments, beacons can be sent according to an IEEE 802.11 wireless standard (i.e., WLAN) and/or a Bluetooth (BT) standard, including Bluetooth low energy (BLE).

In the various embodiments below, like items are referred to by the same reference characters, but with the leading digit(s) corresponding to the figure number.

FIG. 1 is a diagram of a system 100 according to an embodiment. A system 100 can include user devices 102, beacon devices 104, authorities 106, and a server system 108. User devices 102 can register anonymously with the system 100. User devices 102 can be any suitable device having wireless communication and data logging capabilities, including but not limited to, portable electronic device such as smartphones or wearable electronic devices. A user device 102 can receive and store a user ID 110-0 and generate a user record 112. A user record 112 can generate entries by accumulating data from beacons 114 issued from beacon devices 104.

Beacon devices 104 can also register anonymously with the system 100, and can be any suitable electronic device having wireless communication and payload encryption capabilities. Beacon devices 104 can store and receive a beacon ID 110-1, public key 116-0 and a corresponding key ID 118. A beacon device 104 can generate beacon payload data by encrypting a beacon ID, beacon time, and beacon location with the public key 116-0. To such encrypted data, a beacon device 104 can add unencrypted data including the key ID 118, beacon time, and beacon location. Such payload data can be transmitted according to one or more wireless standards. It is understood that the term "beacon" should not be construed as being limited to any particular wireless protocol or standard. A beacon 114 is understood to be wireless transmission having an identifier recognizable by user devices operating according to the wireless standard. In some embodiments, beacons 114 can advantageously utilize existing features of a wireless standard. In some embodiments, beacons 114 can be identified as WLAN beacons (e.g., via frame control field). In addition or alternatively, beacons 114 can be transmitted as advertising beacons on one or more BLE advertising channels.

It is noted that user devices 102 and beacon devices 104 are not mutually exclusive. A user device 102 can also be a beacon device 104, and vice versa. A beacon device can broadcast beacons at high frequency, such that nearby user devices can detect its beacons. A user device may elect to not broadcast beacons at all for privacy. If a user device broadcasts beacons, it may broadcast at a relatively low frequency to save power.

Authorities 106 can be authenticated with the server system 108. This is in contrast to user and beacon devices 102/104 which can remain anonymous to the server system 108. Authorities 106 can serve as intermediaries between user devices 102 and the server system 108. In an alert event, a user 102 can request a token from an authority 106. In response, an authority 106 can contact and receive a token 120 from the server system 108. The authority 106 can "blindly" forward the token 120 to the requesting user device 102. In blindly forwarding the token 120, and authority 106 will not retain the token 120. In some embodiments, an authority can be a medical entity, such as a medical practice or health care provider, or a law enforcement entity, as but two examples.

A server system 108 can include one or more computing devices in communication with user devices 102, beacon devices 104 and authorities 106 over a network 122, which can include the Internet. A server system 108 can include private keys 116-1, a user database 124, a tracing function 126, and a token generator 128. Private keys 116-1 can correspond to public keys 116-0, with matching public/private keys sharing a key ID 118. A user database 124 can include beacon data accumulated from multiple user devices 102 (and optionally beacon devices 104 having user device functionality). A tracing function 126 can search user database 124. Token generator 128 can generate tokens upon request from an authority 106.

In a data acquisition operation, user devices 102 can detect beacons 114 emitted from beacon devices 104. If a beacon 114 has a suitable unencrypted time (and optionally location), user device 102 can store 130-0 the beacon data in a user record 112 with its user ID 110-0. Periodically, a user device 102 can transmit its user record 112 to server system 108. Using key IDs 118, server system 108 can decrypt data in user records 112 and integrate them into a user data base 130-1, if such user record data are valid.

In an alert operation, a user can contact an authority 106 (e.g., with the corresponding user device 102) and request a token 120. Such a request may or may not occur via network 122. In response, an authority 106 can request a token from server system 108 via a connection in which it is authenticated to the server system 108. Server system 108 can generate and provide a token 130-2 authority 106. Authority 106 can send the token 120 to a user (e.g., to a user device 102). A user device 102 can then submit an alert 130-3, with a user ID and token 120 to server system 108. If a server system 108 considers the token valid, a tracing operation 126 can be executed on the user database 124 to identify any other users who were in proximity to the alerting user within a given time period. Such other users can then be notified of the alert. Such notification can be when the other user device next contacts the server system 108.

Figure 2:
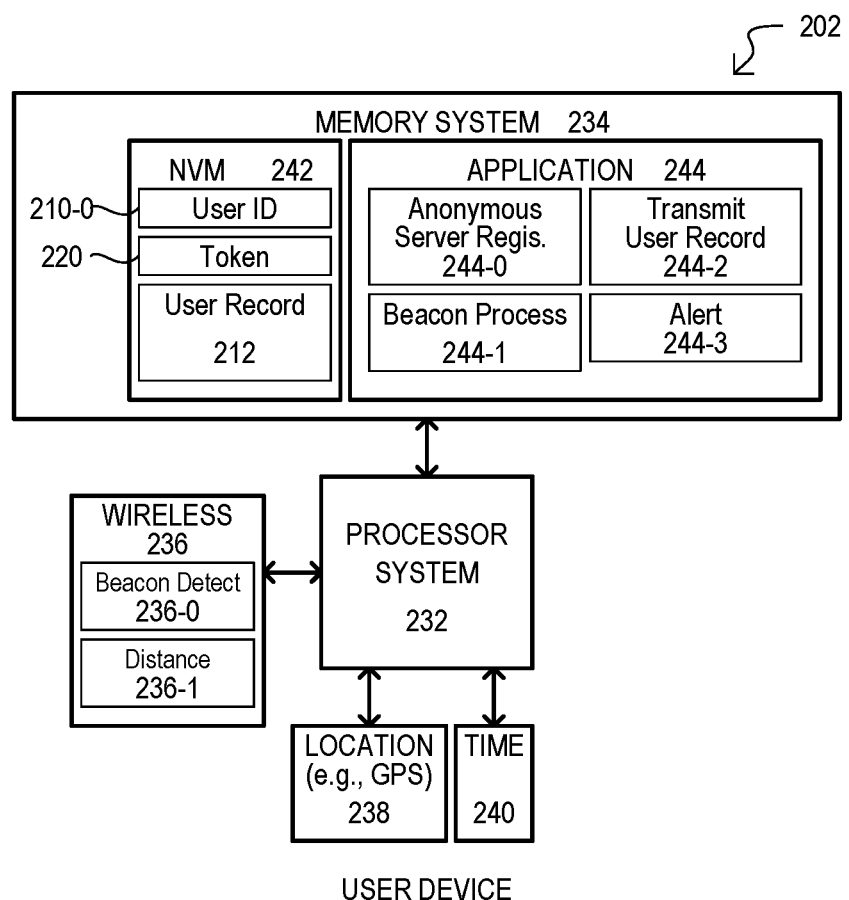
FIG. 2 is a block diagram of a user device according to an embodiment.

FIG. 2 is a block diagram of a user device 202 according to an embodiment. A user device 202 can include a processor system 232, memory system 234, wireless circuits 236, location circuits 238 and a time circuits 240. A processor system 232 can include one or more processors that can execute instructions stored in a memory system 234 to perform various functions, where such functions can be part of one or more applications (apps).

A memory system 234 can include a nonvolatile memory NVM 242 and can store a user application 244. NVM 242 can store a user ID 210-0, a token 220, and a user record 212. A user ID 210-0 can be received when a user device 202 registers with a server system (not shown). A token 220 can be received with a user requests a token (e.g., for an alert event) from an authority (not shown). A user record 212 can be accumulated data from beacons sensed by user device 202.

A user application 244 can include instructions executable by processing system 232 to perform various operations of a close contact or similar tracing system. A user application 244 can include an anonymous registration function 244-0, a beacon processing function 244-1, a record transmitting function 244-2, and an alert function 244-3. Such functions are be described in more detail herein. A user application 244 can be stored in NVM 242 and executed from NVM 242, or loaded into a volatile memory (not shown) for execution.

Wireless circuits 236 can transmit and receive data according to one or more wireless protocols or standards. In some embodiments, wireless circuits 236 can include beacon detect circuits 236-0 which can detect beacons emitted by a beacon device. As but two of many possible examples, beacon detect circuits 236-0 can monitor a particular channel (e.g., advertising channel) for signals and/or beacon detect circuits 236-0 can detect predetermined field values of received packet. In some embodiments, wireless circuits 236 include distance measuring circuits 236-1. Distance measuring circuits 236-1 can measure a distance to a source of a wireless signal, including a distance to a beacon device.

A user device 202 can also include location circuits 238 and time circuits 240. Location circuits 238 can periodically determine a position of a user device 202, and can use any suitable measurement method, including but not limited to assisted global position system or WiFi positioning. Time circuits 240 can maintain a time for a user device and may or may not be part of processing system 232.

Figure 3A:
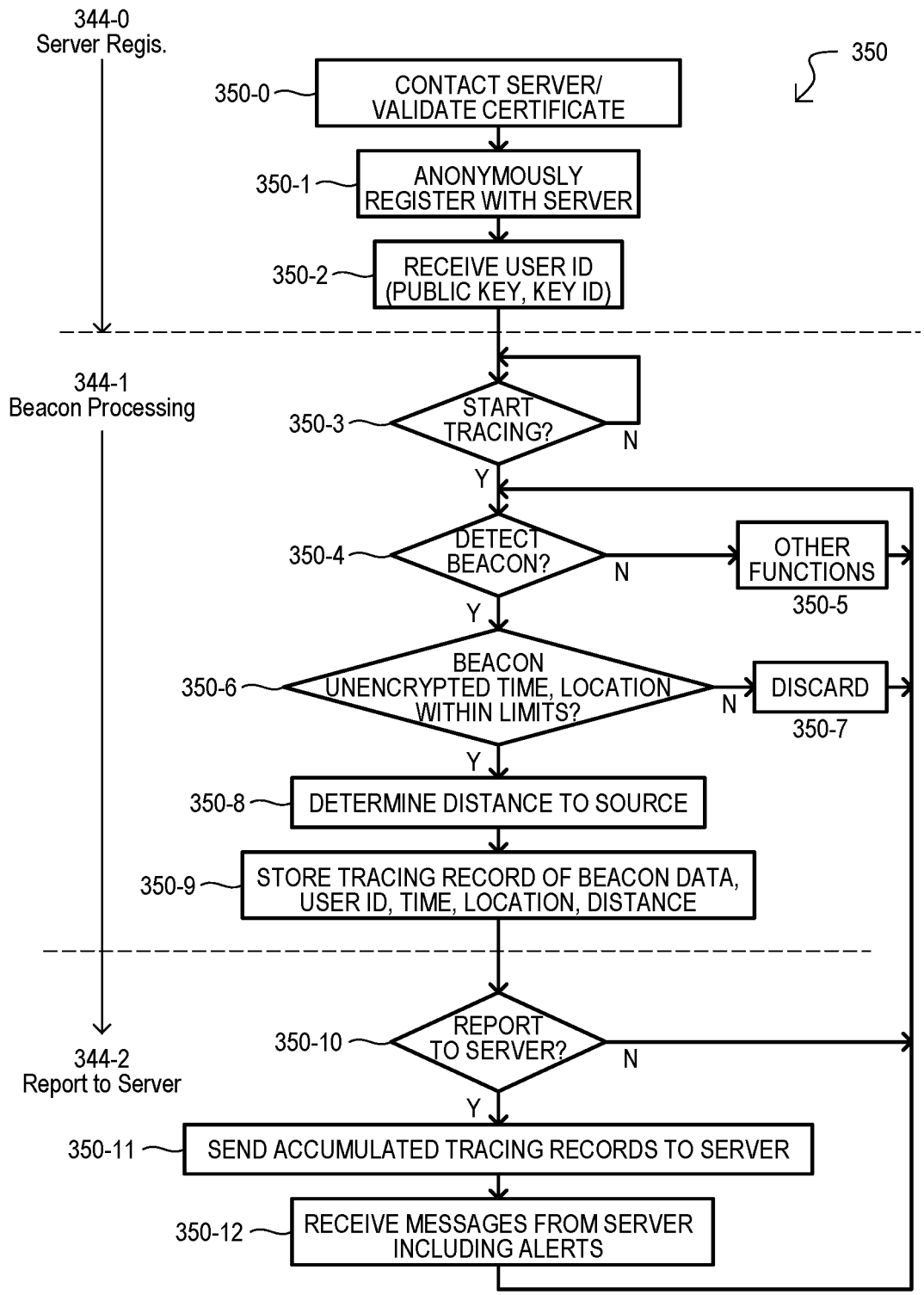
FIGS. 3A and 3B are flow diagrams of user device methods according to embodiments.

FIG. 3A shows user device methods 350 according to embodiments. Methods 350 can include a server registration section 344-0, beacon processing section 344-1, and report to server section 344-2. A server registration section 344-0 can include a user device contacting a server system according to any suitable protocol and validating a certificate of the server system 350-0. Upon confirming the authenticity of the server, a user device can anonymously register with the server 350-1. In response to such registration, a user device can receive a user ID 350-2. In embodiments in which a user device can also function as a beacon device, a user device may also receive a public key and corresponding key ID from a server.

A beacon processing section 344-1 can include a tracing capability 350-3. Such an action can enable a user device to start receiving and recording beacon data. In some embodiments, such an action can include an app on a user's phone being started or enabled. A method 350 can monitor for wireless signals according to one or more protocols to detect a beacon (i.e., a beacon according to the tracking system) 350-4. In some embodiments, a user device can monitor for a WLAN beacon packet and/or monitoring a BLE advertising channel for advertising packets. While a beacon is not detected (N from 350-4), a method 350 can execute other functions of the user device 350-5.

If a beacon is detected (Y from 350-4), a method 350 can examine the beacon for unencrypted time and location values 350-6. If such values are outside of predetermined limits (N from 350-6), a method 350 can discard the beacon data 350-7. While FIG. 3A shows a method 350 that examines both unencrypted time and location data, in some embodiments, location data may not be examined.

If unencrypted time (and location) values are within predetermined limits (Y from 350-6), a method 350 can determine a distance to the beacon source 350-8. Such an action can include using one or more wireless signal measurement techniques. In some embodiments, a beacon can be a WLAN compatible beacon, and a user device can perform a fine time measurement (FTM) to determine distance. In addition or alternatively, a beacon can be a BLE advertising packet, and a user device can perform an angle of arrival measurement (AoA) to generate a distance value. A user device can store a tracing record 350-9. Such a tracing record can include beacon data, which can include encrypted data (e.g., beacon ID, time, location) and unencrypted data, including the user id, the distance value, as well as time and location. Such tracing records can be stored in a NVM of a user device.

A report to server section 344-2 can include determining when it is time to report to the server 350-10. Reporting can occur according to any suitable criteria, including but not limited to, reporting with a predetermined frequency and/or reporting when tracing records reach a certain size. If reporting is not to occur (N from 350-10), a method 350 can continue to detect beacons (350-4). If reporting is to occur (Y from 350-10), a method 350 can include sending accumulated tracing records to the server 350-11. A user device can also receive messages from the server, including alerts 350-12. In some embodiments, such an action can include a server determining a user ID from uploaded tracing data, and then checking to see if any alerts have been used for the user ID.

Figure 3B:
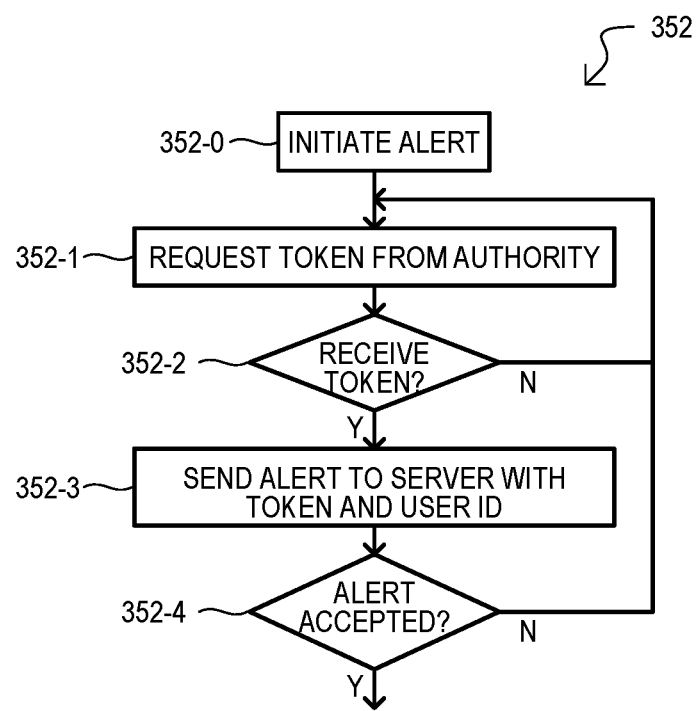

FIG. 3B shows additional user device methods 352 according to embodiments. Methods 352 can include a user initiating an alert 352-0. Such an action can vary according to the particular system application. As but a few of many possible examples, a user may determine they have been exposed to or have contracted a communicable disease, a user may have lost an item, or a user may be investigating an event, such a crime or accident.

A user can request a token from an authority 352-1. In some embodiments, such an action can include a user contacting an authority via a user device. A method 352 can determine if a token is received 352-2 from the authority. If a token is not received (N from 350-2), a method 352 can return to 350-1 to repeat a request. If a token is received (Y from 350-2), a user can send an alert to the server system with the token and user ID 352-3. A method 352 can determine if the alert has been accepted by the server 352-4. If the alert is not accepted (e.g., the token is expired), a method 352 can return to 350-1 to repeat a request.

Figure 4:
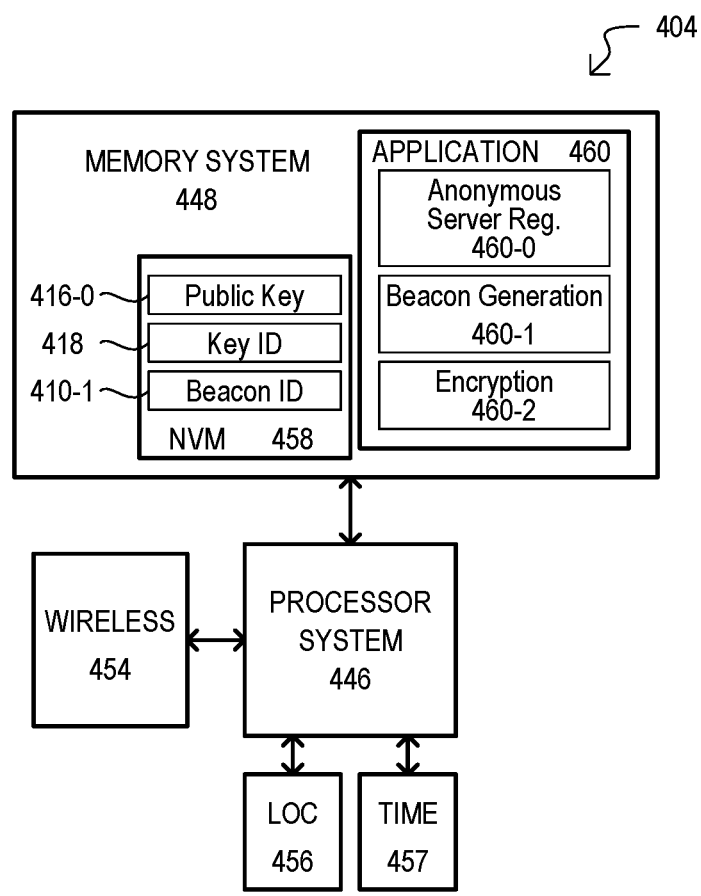
FIG. 4 is a block diagram of a beacon device according to an embodiment.

FIG. 4 is a block diagram of a beacon device 404 according to an embodiment. A beacon device 404 can include a processor system 446, memory system 448, wireless circuits 454, location circuits 456 and a time circuits 457. A processor system 446 can include one or more processors that can execute instructions stored in a memory system 448.

A memory system 448 can include a NVM 458 and can store a beacon application 460. NVM 460 can store a public key 416-0, a key ID 418, and a beacon ID 410-1. A public key 416-0 can be an encryption key for generating beacon data. Public key 416-0 can be received when the beacon device 404 registers with a server system. A key ID 418 can identify a public/private key pair. That is, one can determine which private key to use in a decryption operation based on a key ID.

A beacon application 460 can include instructions executable by processing system 446 to perform various beacon device functions. A beacon application 460 can include an anonymous registration function 460-0, a beacon generation function 460-1, and encryption functions 460-2. Such functions are be described in more detail herein. A beacon application 460 can be stored in NVM 458 and executed from NVM 458, or loaded into a volatile memory (not shown) for execution.

Wireless circuits 454 can transmit and receive data according to one or more wireless protocols or standards. Location and time circuits 456 and 457 can operate as described for FIG. 2 (items 238 and 240).

As noted above, a user device can also be a beacon device and vice versa. A user device could, in addition to accumulating beacon data from other beacon devices, transmit beacons itself. In such cases, a beacon ID would be the same as a user ID. Likewise, a beacon device can be a user device, accumulating beacons from other devices, and periodically transmitting them to a server system for integration into a user database. In such cases a user ID would be the beacon ID.

Figure 5:
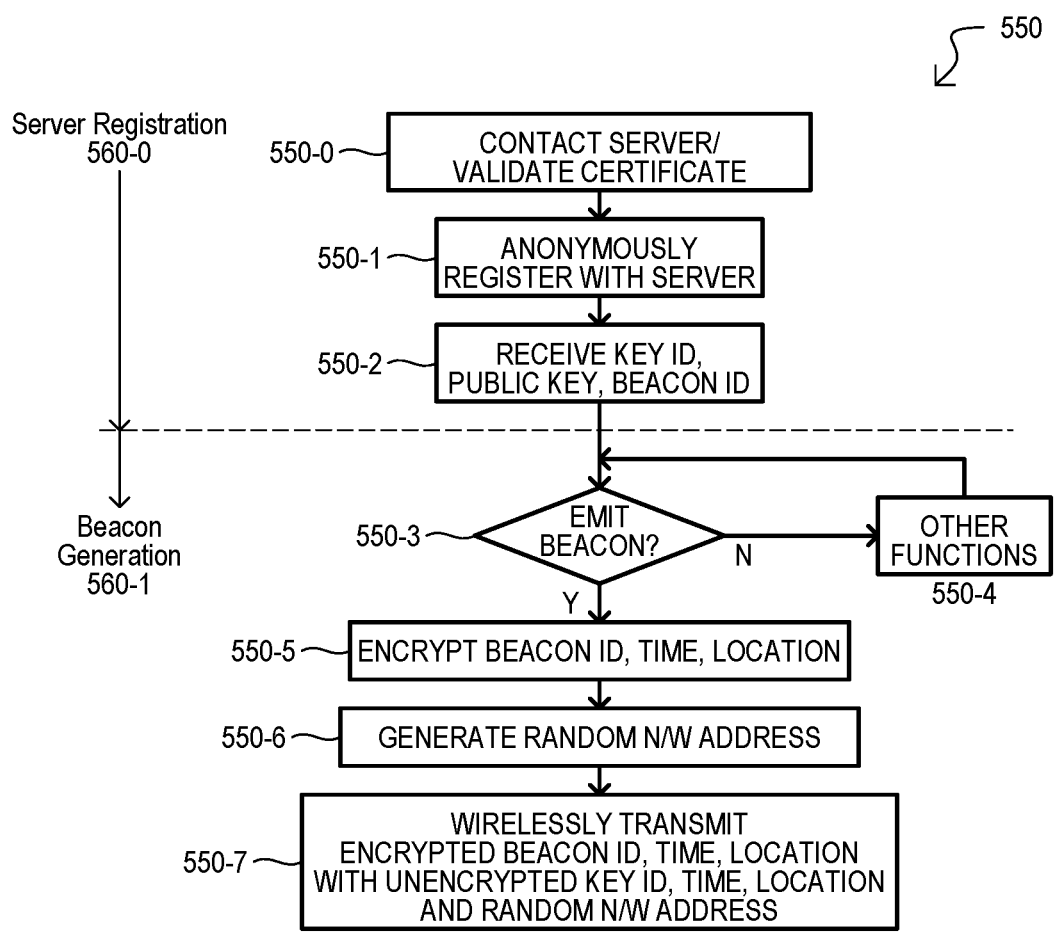
FIG. 5 is a flow diagram of a beacon method according to an embodiment.

FIG. 5 shows beacon device methods 550 according to embodiments. Methods 550 can include a server registration section 560-0 and beacon generation section 560-1. A server registration section 560-0 can include actions like those shown for user device (FIG. 3A, 344-0). However, unlike the user device methods, in response to an anonymous registration, a beacon device can receive a key ID, a public key, and a beacon ID from the server 550-2.

A beacon generation section 560-1 can include determining if a beacon is to be emitted 550-3. Such an action can include a beacon device 560-1 operating to broadcasting a beacon with a predetermined periodicity. In some embodiments, such an action can include utilizing a beacon transmission of a preexisting protocol (e.g., WLAN access point (AP) beacon). The preexisting beacon can be is modified to include beacon information as described herein. While a beacon is not to be emitted (N from 550-3), a method 550 can execute other functions of the beacon device 550-4.

If a beacon is to be emitted (Y from 550-3), a method 550 can encrypt a beacon ID, time value and location value 550-5. Such an action can include a beacon device encrypting such data values with the public key received from a server system. A beacon device can generate a random network address 550-6. Such an action can include generating a random address compatible with a protocol used to transmit the beacon. As but one example, a beacon device can generate a random MAC address. Such an action can help ensure the anonymity of users of the system. A method 550 can then transmit the encrypted beacon ID, time and location values, along with unencrypted key ID, time and location values, with the random network address 550-7. Such an action can include transmitting such data according to any suitable method protocol, including but not limited to WLAN and/or BLE.

Figure 6:
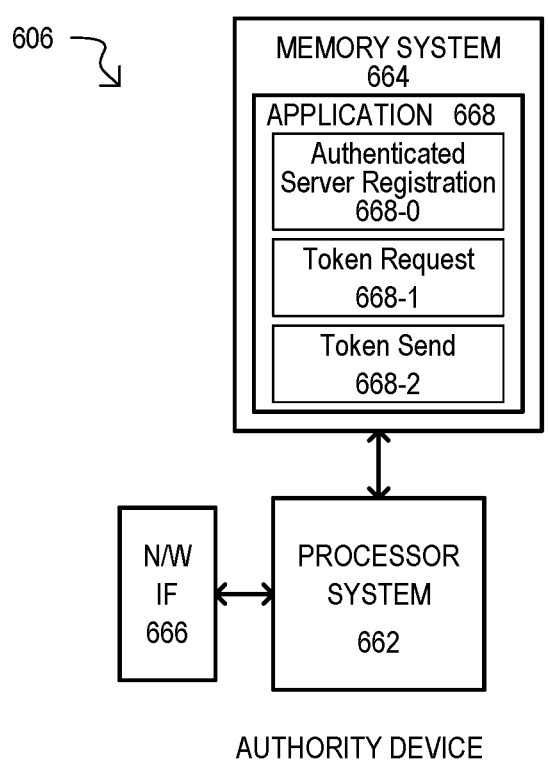
FIG. 6 is a block diagram of an authority device according to an embodiment.

FIG. 6 is a block diagram of an authority device 606 according to an embodiment. An authority device 606 can include a processor system 662, a memory system 664, and network interface 666. A processor system 662 can include one or more processors that can execute instructions stored in a memory system 664.

A memory system 664 can include an authority application 664 having instructions executable by processing system 662 to perform various authority device functions. An authority application 664 can include an authenticated registration function 668-0, a token request function 668-1, and a token send function 668-2. Such functions are be described in more detail herein.

A network interface 666 can provide a network connection to enable communication with users and a server system. A network interface 666 can be a wired and/or wireless connection.

Figure 7:
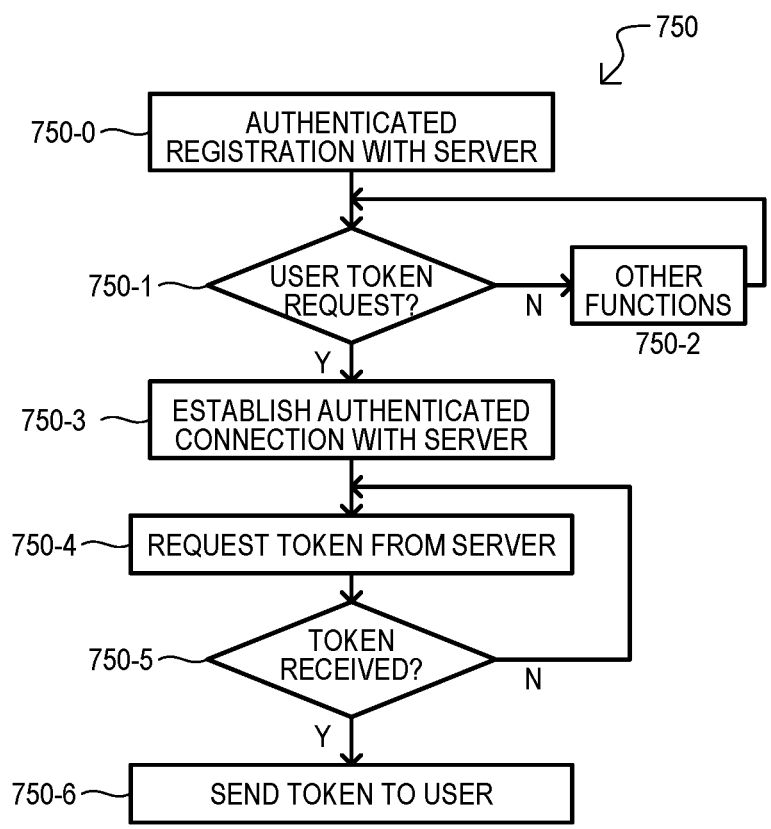
FIG. 7 is a flow diagram of an authority method according to an embodiment.

FIG. 7 shows an authority device method 750 according to an embodiment. A method 750 can include an authenticated registration with a server 750-0. Such an action is in contrast to the registration of user devices and beacon devices, which are anonymous. Such an action can ensure that an authority is an appropriate entity for issuing tokens (which in turn can cause a system to generate alerts). While an authority device waits for a token request (N from 750-1), it can execute other functions 750-2.

Upon receiving a user token request (Y from 750-1), an authority can establish an authenticated connection with a server 750-3. An authority can request a token from a server 750-4. If a token is not received (N from 750-5), an authority can continue to request tokens from a server. Upon receiving a token (Y from 750-5), a method can send the received token to the requesting user 750-6.

Figure 8:
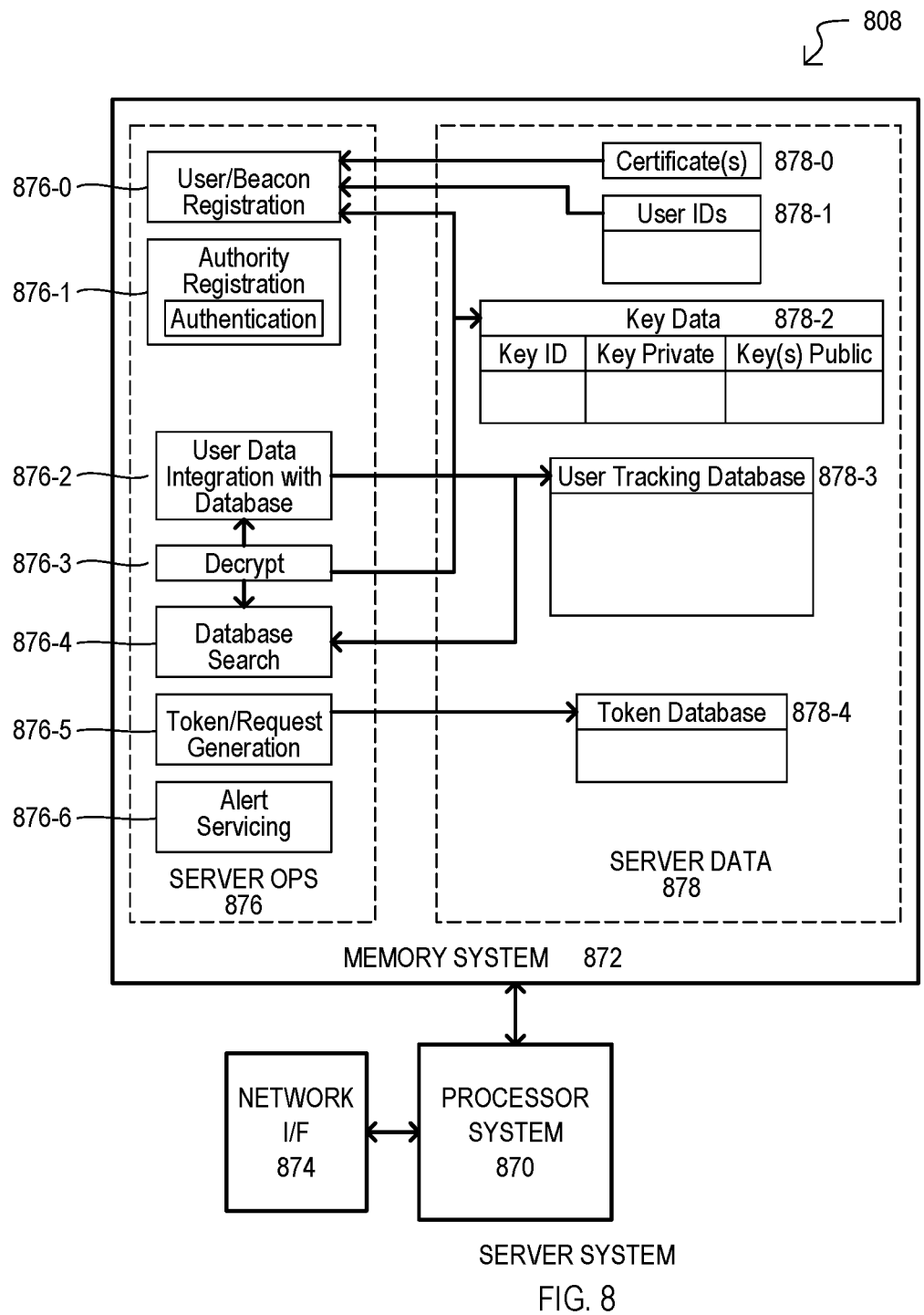
FIG. 8 is a block diagram of a server system according to an embodiment.

FIG. 8 is a block diagram of a server system 808 according to an embodiment. A server device 808 can include a processor system 870, a memory system 872, and network interface 874. A processor system 870 can include one or more processors that can execute instructions stored in a memory system 872.

A memory system 872 can include server operations 876 and server data 878. Server operations 876 can include user/beacon registration 876-0, authority registration 876-1, user data integration 876-2, decryption 876-3, data base search 876-4, token request/generation 876-5, and an alert servicing 876-6. Such operations are be described in more detail herein.

Server data 878 can include a certificate data 878-0, user IDs 878-1, key data 878-2, database 878-3, and tokens 878-4. Certificate data 878-0 can be used for user and beacon devices to authenticate the server system 808. User IDs 878-1 can be stored or generated values transmitted to devices upon registration. User IDs 878-1 can include user IDs for user devices and beacon IDs for beacon devices. Key data 878-2 can include private keys, corresponding public keys, and key IDs that identify private keys. A user database 878-3 can include user records uploaded by user devices and can be searched with a database search operation 876-4. Tokens 878-4 can be tokens that have been generated by a token generation function 876-5 and stored.

Figure 9A:
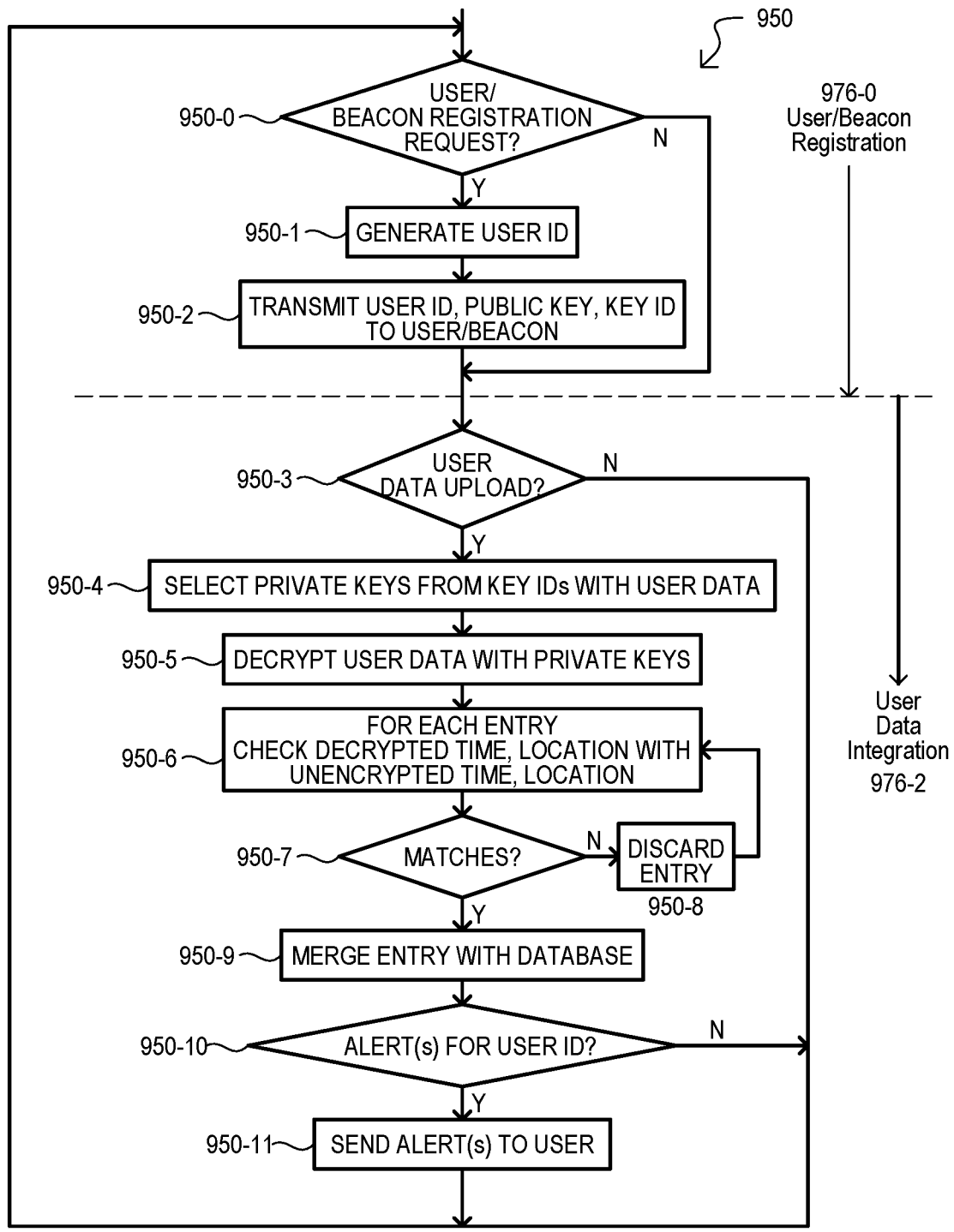
FIGS. 9A, 9B and 9C are flow diagrams of server system methods according to embodiments.

FIG. 9A shows server methods 950 according to embodiments. Methods 950 can include a user/beacon registration section 976-0 and user data integration section 976-2. A user/beacon registration 976-0 can include receiving a user or beacon registration request 950-0. Such an action can include receiving a request from a user or beacon device from an app stored on such a device. In some embodiments, such an action can include a server system providing a certificate to prove its authenticity to the user or beacon device. As noted herein, a server system does not authenticate a user or beacon device, as such devices can register anonymously. A server system can generate a user or beacon ID value 950-1. Such an action can include but is not limited to: generating an ID value according to an algorithm, randomly selecting an ID value from a pool of such values, or a combination thereof. The generated user or beacon ID value can be transmitted to the requesting user/beacon device 950-2.

A user data integration section 976-2 can include determining if user data is to be uploaded 950-3. Such an action can include a user device contacting the server and providing user data for upload. A user device can then transmit a user record to the server system. A user record can include contact entries that each include a user ID, unencrypted key ID, time and location, and encrypted data. A server system can select private keys based on key IDs from the user record 950-4 and decrypt encrypted data with such keys 950-5. In some embodiments, such operations can provide decrypted time and location data. Such decrypted time and location data can be compared with the unencrypted time and location data 950-6. If decrypted values are not within a predetermined range of corresponding unencrypted values (N from 950-7), the entry can be discarded 950-8. Such an operation can prevent replay attacks on the server system. As noted herein, other embodiments may not compare decrypted location values with unencrypted location values.

If the decrypted values match the corresponding unencrypted values (Y from 950-7), the entry can be merged with a server database 950-9. In the embodiment shown, a method 950 can also include a server system checking for any alerts for the user ID 950-10. If no such alert exists (N from 950-10), a method 950 can continue (including returning to 950-0). If an alert exists (Y from 950-10), a method 950 can send the alert to the user 950-11.

Figure 9B:
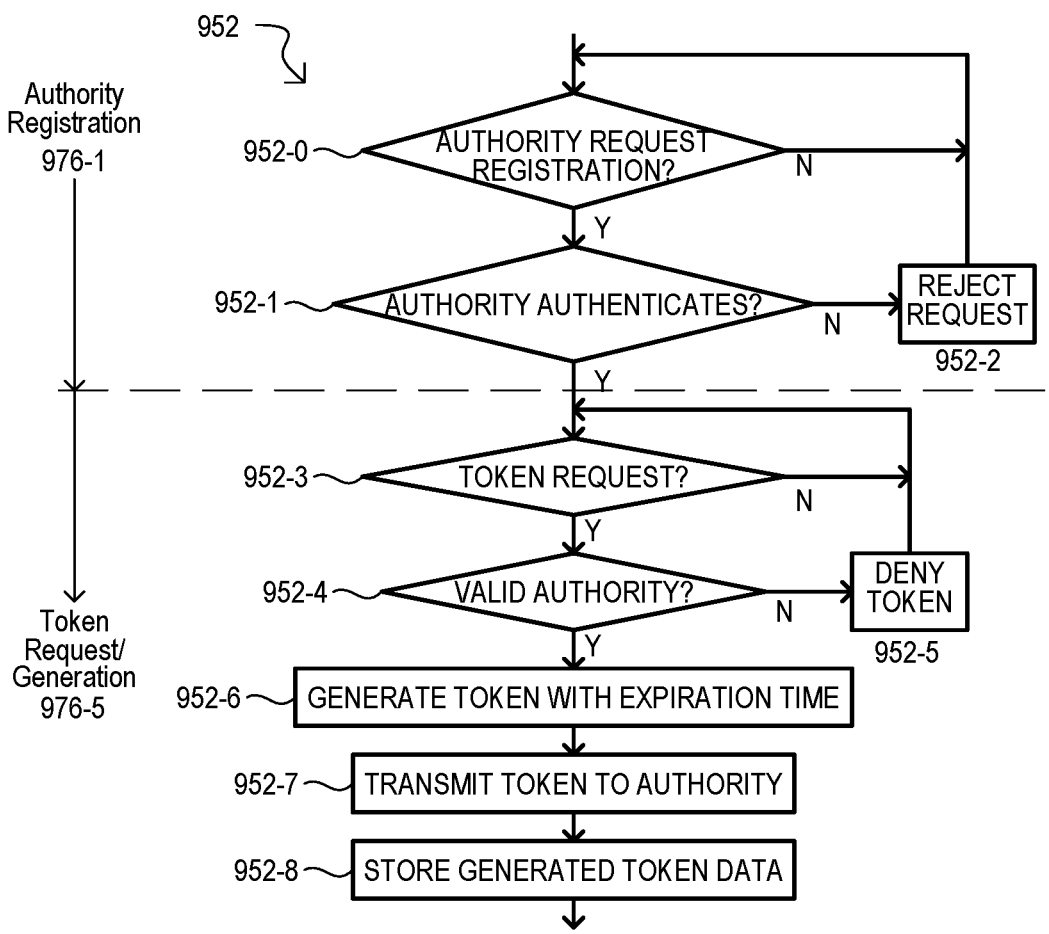

FIG. 9B shows additional authority server system methods 952 according to embodiments. A method 952 can include authority registration section 976-1 and a token request/generation section 976-5. An authority registration section 976-1 can include receiving a request from an authority to register with the server system 952-0. Upon receiving such a request (Y from 952-0), a method 952 can execute an authentication process to verify the authenticity of the authority 952-1. Such an action can include any suitable authentication method and can vary according to the type of authority. If an authority fails authentication (N from 952-1), the request can be rejected 952-2.

A token request/generation section 976-5 can include determining if a token request is being made by an authority 952-3. Such an action can include receiving a request from a purported authority for a token. If a token request is received (Y from 952-3), a method 952 can determine if the requisition authority has been previously authenticated 952-4. Such an action can include determining if the requesting authority has previously registered with the server system. If the requester is determined not to be valid (N from 952-4), a method 952 can deny the request 952-5. In some embodiments, a method 952 can then direct the requester to an invitation to register with the server system.

If the requester is determined to be valid (Y from 952-4), a method 952 can generate a token with an expiration time 952-6. The token can be transmitted to the authority 952-7. The generated token can then be stored by the server system 952-8. According to embodiments, a server system 952 will maintain no record of which token goes to which authority.

Figure 9C:
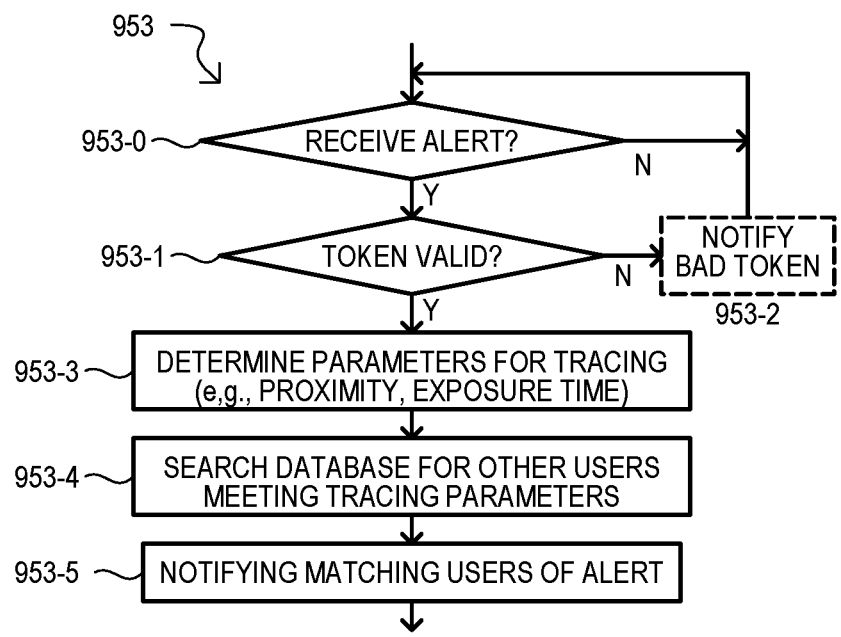

FIG. 9C shows an alert servicing method 953 for a server system according to an embodiment. A method 953 can include determining if an alert is being received 953-0. Such an action can include receiving an alert communication from a user device, via an application or the like, running on the user device. A method 953 can determine if the alert received includes a valid token 953-1. Such an action can include a server system checking a received token against those previously issued. As noted herein, tokens can have an expiration time, and an expired token is an invalid token. If a token is determined to be invalid (N from 953-1), a method 953 can optionally notify the requester that the token is not valid 953-2 (e.g., if the token was issued but now expired).

If a token is determined to be valid (Y from 953-1), a method 953 can determine parameters for a tracing operation 953-3. In some embodiments, such parameters can be established ahead of time for each database. However, in other embodiments, such parameters can be received from an authority, a user, or another source. A server system can search a database for other user IDs meeting the tracing parameters 953-4. Users meeting the tracing parameters 953-4 can be notified of the alert 953-5. Such an action can include notifying a corresponding user device the next time it uploads its user records, or otherwise contacts the server system.

Figure 10:
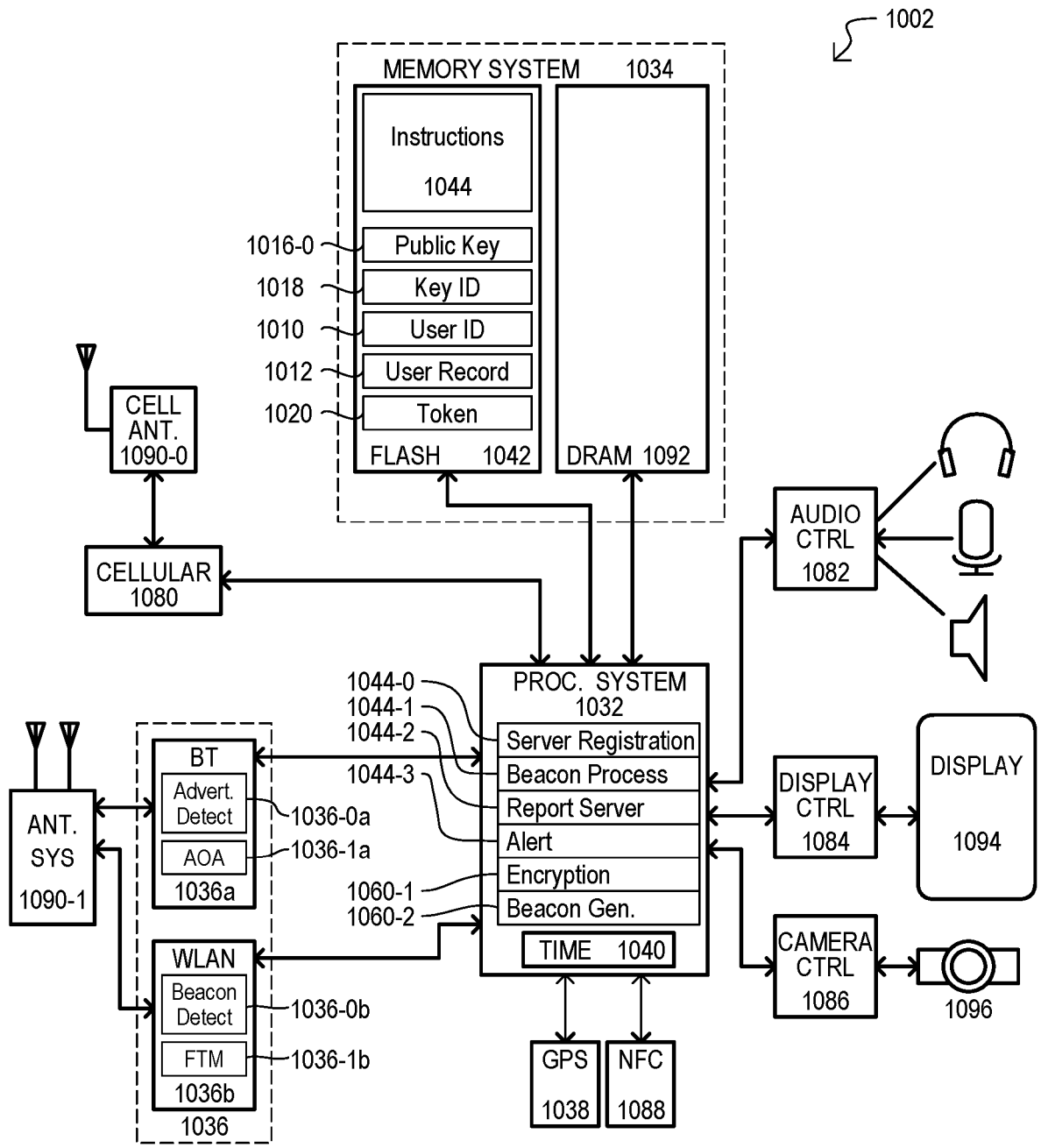
FIG. 10 is a block diagram of a device according to another embodiment.

FIG. 10 is a block diagram of a device 1002 according to another embodiment. A device 1002 can be a portable electronic device, such as a smartphone, or the like. A device 1002 can operate as a user device and/or a beacon device. A device 1002 can include a processor system 1032, a memory system 1034, wireless circuits 1036, positioning circuits 1038, cellular circuits 1080, audio control circuits 1082, display control circuits 1084, camera control circuits 1086, and near field communication (NFC) circuits 1088.

A processor system 1032 can take the form of any of those described herein, or equivalents, and can provide various functions according to instructions 1044 stored in memory system. Instructions 1044 can include, but are not limited to, an operating system and one or more applications that employ preexisting functions available through the operating system. Functions provided by a processing system 1032 can include, but not limited to, a registration function 1044-0, a beacon processing function 1044-1, a server reporting function 1044-2, an alert function 1044-3, encryption functions 1060-1, and beacon generation functions 1060-2. Such functions can take the form of any of those described herein, or equivalents. A processor system 1032 can also include time circuits 1040.

A memory system 1034 can include nonvolatile "flash" memory 1042 and volatile dynamic random access memory (DRAM) 1092. Flash memory 1042 can store various values for executing close contact tracing operations described herein, as well as various other functions. Stored values can include, but are not limited to, instructions 1044 (including an operating system and applications), a public key 1016-0, a key ID 1018, user ID 1010, user record 1012, and token(s) 1020. Such values can take the form of any of those described herein or equivalents.

Wireless circuits 1036 can include BT circuits 1036*a* and WLAN circuits 1036*b*. BT circuits 1036*a* can be compatible with one or more BT standards, including BLE. BT circuits 1036*a* can include BT advertising detection functions 1036-0*a* and AoA functions 1036-1*a*. BT advertising detection functions 1036-0*a* can detect beacon packets transmitted on a BT compatible advertising channel. AoA functions 1036-0*a* can determine a distance from the device 1002 to a BT beacon source. WLAN circuits 1036*b* can be compatible with one or more WLAN standards. WLAN circuits 1036*b* can include beacon detect functions 1036-0*b* and FTM functions 1036-1*b*. Beacon detect functions 1036-0*b* can detect WLAN beacon packets. FTM functions 1036-0*b* can determine a distance from a WLAN beacon source. In some embodiments, wireless circuits 1036 can be part of a combination integrated circuit device. Wireless circuits 1036 can be connected to an antenna system 1090-1.

Cellular circuits 1080 can provide communication functions according to one or more cellular standards and can be connected to a cellular antenna system 1090-0. GPS circuits 1038 can determine a location of a device 1002. NFC circuits 1088 can provide NFC capabilities for the device 1002. Audio control circuits 1062 can provide audio functions for the device 1002. Display control circuit 1084 can control a display 1094 of the device 1002, which an also serve as a user input (e.g., a touchscreen). A camera control circuit 1086 can control a camera 1096.

In some embodiments, at least a processor system 1032, memory system 1034, and wireless circuits 1036 can be formed by a system-on-chip (SoC) type device.

While beacon packets according to embodiments can take any suitable format according to the wireless protocol or standard used, particular packets according to some embodiments will now be described.

Figure 11A:
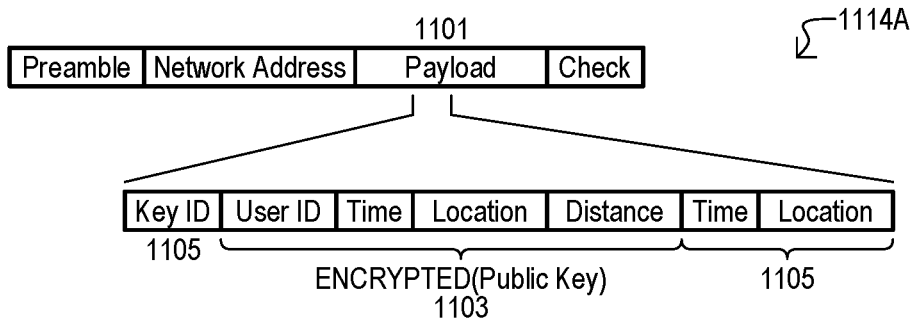
FIGS. 11A, 11B and 11C are diagrams of beacons according to embodiments.

FIG. 11A is a diagram showing a beacon packet 1114A according to an embodiment. A beacon packet 1114A can include various packet fields, including a preamble, network address, payload 1101 and check field. A payload 1101 can include encrypted data 1103 and unencrypted data 1105. Unencrypted data 1105 can include a key ID, a time value and a location value. Encrypted data 1103 can include a user ID (or beacon ID), the time value, the location value, and a distance value. Encrypted data 1103 can be encrypted with a public key corresponding to key ID.

Figure 11B:
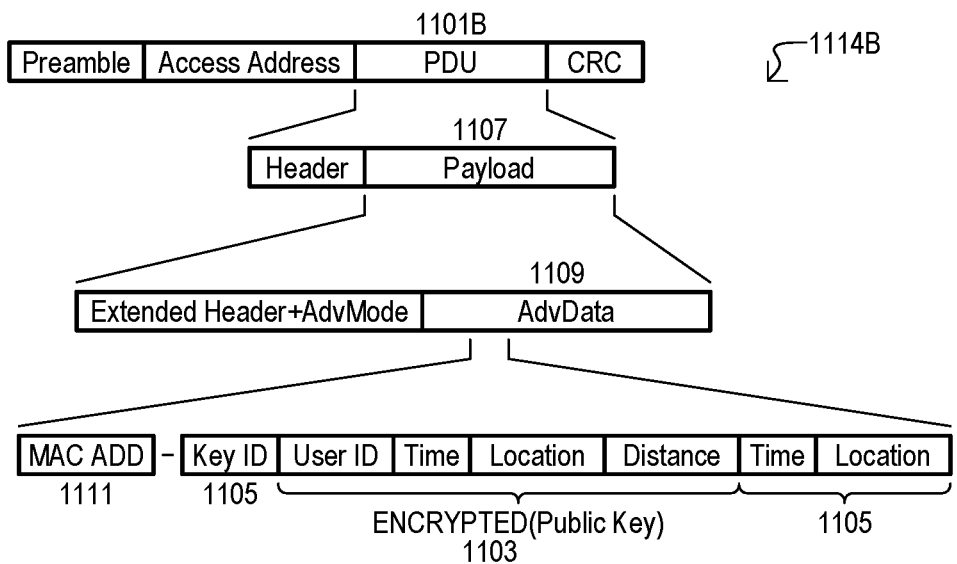

FIG. 11B is a diagram showing a BT packet 1114B according to an embodiment. A BT packet 1114B can have various fields, including preamble, access address, protocol data unit (PDU) 1101B, and CRC. PDU 1101B can include a header and payload 1107. A payload 1107 may include an extended header and advertising data 1109. Advertising data 1109 can include encrypted data 1103 and unencrypted data 1105, as described with reference to FIG. 11A. In some embodiments, advertising data 1109 can also include a MAC address 1111. A MAC address 1111 can be randomized by a beacon device. Other embodiments can include packets according to the iBeacon standard promulgated by Apple, Inc.

Figure 11C:
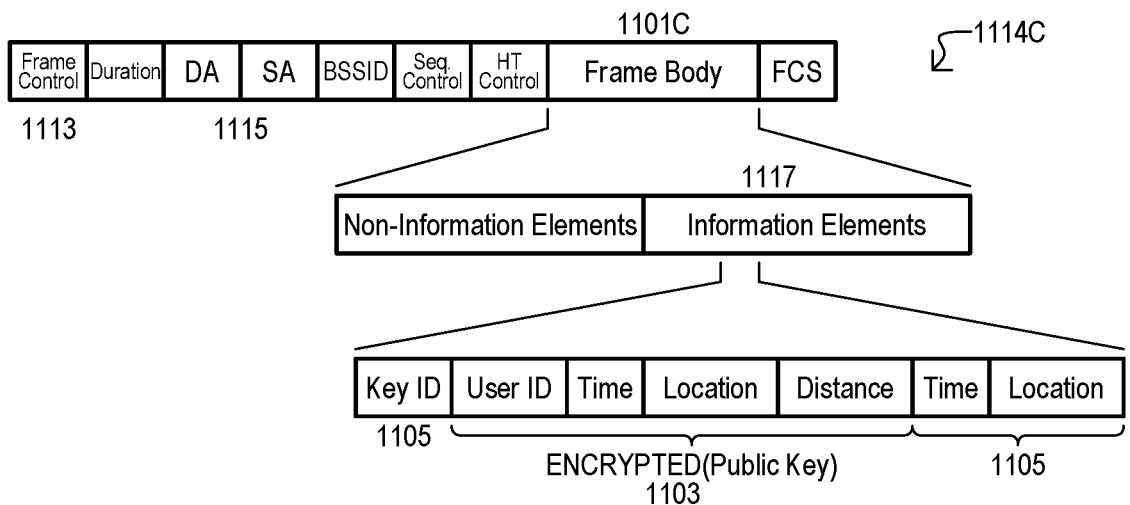

FIG. 11C is a diagram showing a WLAN packet 1114C according to an embodiment. A WLAN packet 1114C can include various fields, including frame control 1113, duration, address 1115, BSSID, sequence control, HT control, a frame body 1101C, and FCS. A frame control field 1113 can identify the WLAN packet 1114C as a beacon packet. Address 1115 can be randomized by a beacon device. A frame body 1101C can include information elements (IEs) 1117 and non-IEs. IEs 1117 can include encrypted data 1103 and unencrypted data 1105, as described with reference to FIG. 11A.

According to embodiments, a tracking system can provide strong privacy protection as users can be anonymous to the tracking server system at all times. A user can register with a server system without user-to-server authentication, receiving a user ID (or beacon ID), a public key, and a key ID identifying the public key. In some embodiments, these parameters can be acquired and stored with a tracking app on a user mobile device.

According to embodiments, a beacon device (or a user device operating as a beacon device) can periodically broadcast beacon data (e.g., key ID, encrypted user ID/time/location, unencrypted time/location) in a beacon, such as a WLAN beacon or BLE advertisement frames. A location can include GPS coordinates, or be derived with associated Wi-Fi/BLE devices, using FTM and AoA techniques. A user device can save observed beacon data broadcast from nearby beacon devices into its NVM, together with its own user ID/time/location. A user device can periodically upload saved user records (e.g., beacon data) to a server system, which can merge the beacon data into a database. The database can thus contain close contact history of all users uploading beacon data. If there are any alerts pending for a user ID uploading the data, the server system can return the alerts to the user device, and thereby notify the user.

According to embodiments, a user may go through an authority to send an alert to a server system. Such a process can prevent hoax alerts, as although the user remains anonymous to a server system, the user is essentially verified by an authority. According to embodiments, an authority can be conceptualized as a special type of user. When an authority registers to a server system, mutual authentication can occur so that the server system can identify and trust the authority. A server system can distribute tokens (e.g., one-time random numbers) to authorities without tracking which authority gets which token. When a user sends an alert to a server system, the user can request a token from the relevant authority. The user can then include the token in the alert sent to the server system. According to embodiments, an authority does not track which token has been given to the user, thus preserving user privacy.

Figure 12:
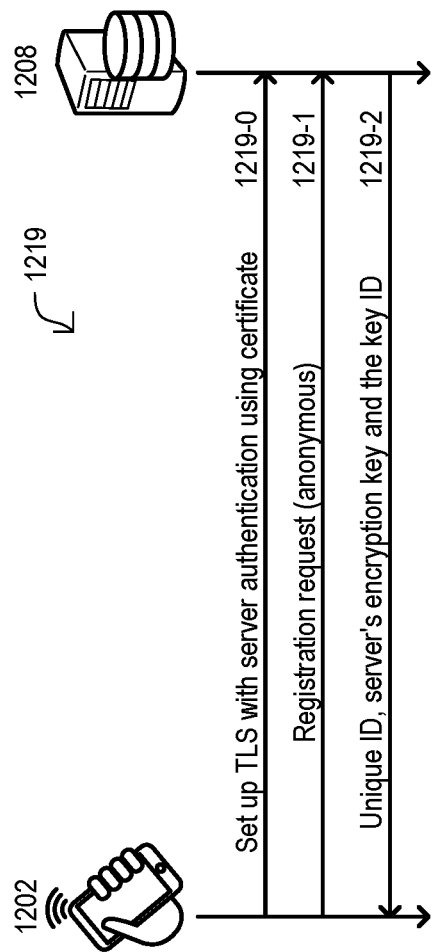
FIG. 12 is a communication diagram of a user/beacon registration operation according to an embodiment.

FIG. 12 is a communication diagram showing a user/beacon registration operation 1219 according to an embodiment. Operation 1219 shows communications between a user/beacon device 1202 and a server system 1208. A user/beacon device 1202 can register with a server system 1208 to acquire and report beacon (e.g., tracking or tracing) data and/or emit beacons of beacon data. A user device can be any suitable device, including but not limited to a smartphone or a wearable device with a WLAN interface, BLE interface, or both. A beacon device can also be a device installed at fixed locations to facilitate the tracing service.

For user device-to-server communication, such as a user/beacon device registration, a server system can authenticate itself to the user device using with a security certificate issued by a well-known certificate authority (CA). However, no user device-to-server authentication can occur (for protecting user privacy). In FIG. 12 a user device 1202 can set up a transport layer security (TLS) type connection, authenticating the server system 1208 with its certificate 1219-0. Upon establishing the connection, a user device 1202 can make a registration request with anonymity 1219-1. During registration, a user device 1202 can receive a unique user (or beacon) ID, a server-generated public key, and a key ID identifying this public key 1219-2. In some embodiments, such values can be installed with a tracking app running on the user device.

Figure 13:
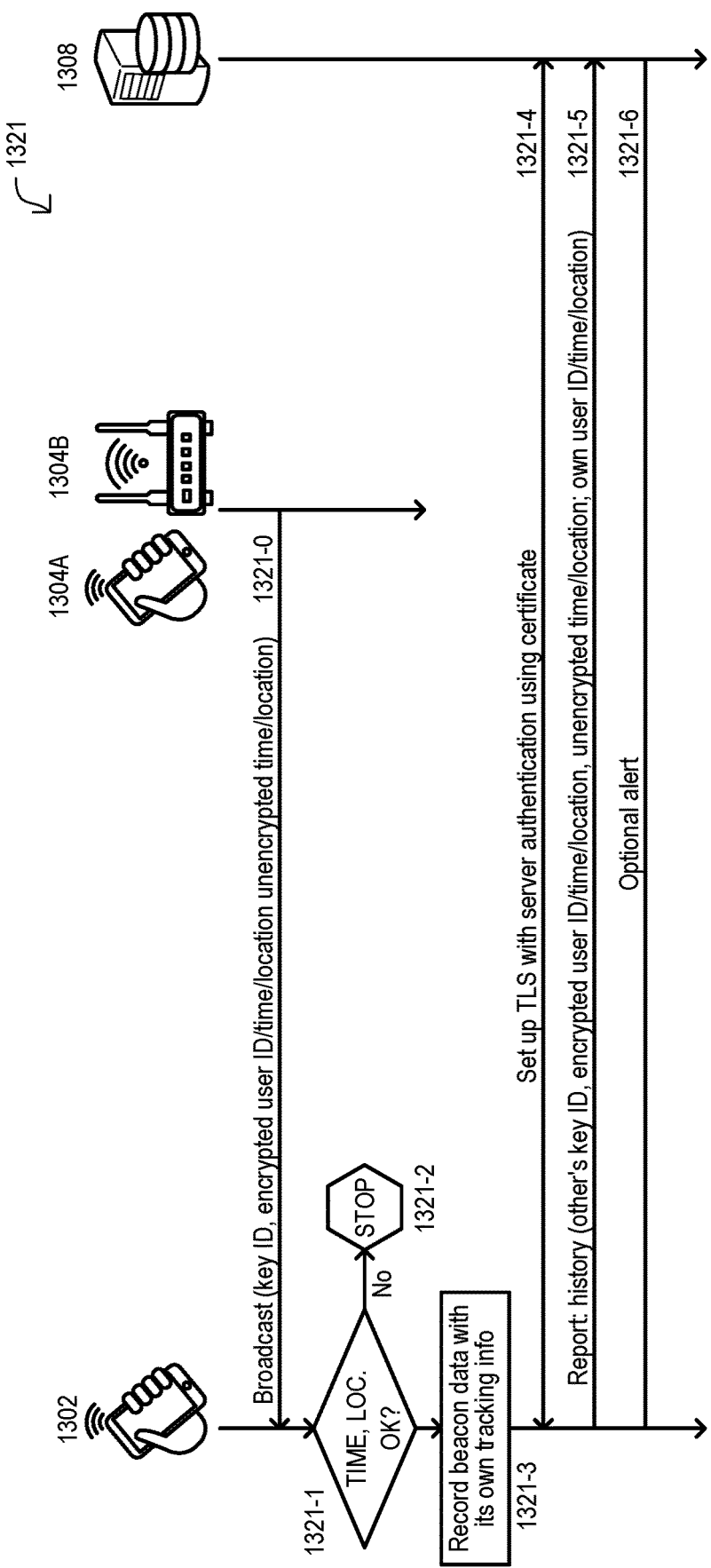
FIG. 13 is a communication diagram of a server reporting operation according to an embodiment.

FIG. 13 is a communication diagram showing a beacon acquisition and server reporting operations 1321 according to embodiments. Operations 1321 show communications between a user device 1302, a beacon device (1304A or 1304B), and a server system 1308. A beacon device 1304A/B can broadcast beacon data 1321-0.

According to embodiments, devices of a system (i.e., user device or beacon device) can piggyback beacon data within communications according to an existing WLAN/BLE protocol for other devices to find. In some embodiments, a WLAN AP can serve as beacon for a tracking system using an existing beacon according to the WLAN standard. Such a WLAN beacon can include: in encrypted form, a user (beacon) ID, current time, and optionally current location. Such values are encrypted with public key identified by the key ID received during registration. The same unencrypted current time, and optionally current location, can also be included in the beacon. A user ID is encrypted for privacy. Current time and current location are encrypted together for preventing a replay attack. Current time and current location are repeated in unencrypted form to enable the listening device (i.e., user device) to validate the observed beacon information using its own time and location, which should be similar.

WLAN stations (STAs) operating as beacon devices can periodically (at a low frequency) turn on for broadcasting beacon data only, and then turn off. As but one example, such a frequency can be no more frequent than a WLAN AP beacon period. In a similar fashion, a BLE compatible device operating as a beacon device can include the above beacon information in an extended advertisement message.

In the various beacons described, location values can include, but are not limited to: GPS coordinates from onboard GPS hardware, a meaningful address configured by the user, or derived location from other devices using WLAN and BLE AoA technologies.

Referring still to FIG. 13, a user device 1302 can observe beacon data from beacon devices. The user device 1302 can verify that a time and location (from the unencrypted beacon data) match its own time and location by a sufficient amount 1321-1. If such values vary by too large an amount, the beacon data processing can stop 1321-2 (i.e., the beacon data is discarded). If time and location values are okay, the beacon data (key ID, encrypted ID/time/location, unencrypted time/location) can be stored along with a user ID/time/location into a history file (e.g., user record) 1321-3.

A user device 1302 can send its history file to the server system 1308 periodically, and then delete the history file to save memory. In FIG. 13 a user device can establish a TLS connection and authenticate the server system 1321-4. When a connection to a server system is established, a user device 1302 can report its history (e.g., send its user records) 1321-5.

According to embodiments, a server system 1308 can decrypt the user ID in tracking records in the uploaded history file using the corresponding private key identified by the key ID. The decrypted time and location can be compared with the unencrypted time and location. If both encrypted and unencrypted time/location match, the tracking record can be merged into the user's accumulated tracking history file (e.g., database). The server system can then check if the user ID has been marked by some alert indications submitted by other users. If it is marked, the corresponding alerts are sent back to the device, and the device notifies the user 1321-6.

If a WLAN interface is used for broadcasting beacon data, the beacon data can be an IE in a beacon. Visible information can include a key ID, the device time, and optionally, the device location. In some embodiments, a key ID can be identical for many users, as a server system may not change public/private key frequently. A MAC address can be randomized for a different MAC address per broadcast. As such, a beacon device cannot be tracked and/or identified based on its beacon data and MAC address. Whenever a user device observes beacon data from another device, the user device can try FTM to measure the distance to the other device, and save the distance as a part of location information. A beacon device can include its location in the broadcast beacon data, and broadcast the beacon at relatively high frequency, such that nearby user devices can detect beacon data while saving power (user devices can be turned on less frequently).

If a BLE interface is used for broadcasting beacon data, beacon data can be an IE in EXT_ADV channel. The BLE beacon can be broadcast at a frequency such that the BLE interface randomizes its MAC address for privacy, with a different MAC address being used per broadcast. Whenever a user device observes beacon data from another device, the user device can use AoA technology to estimate the other BLE device's direction and distance, and save them as a part of its location information.

Figure 14:
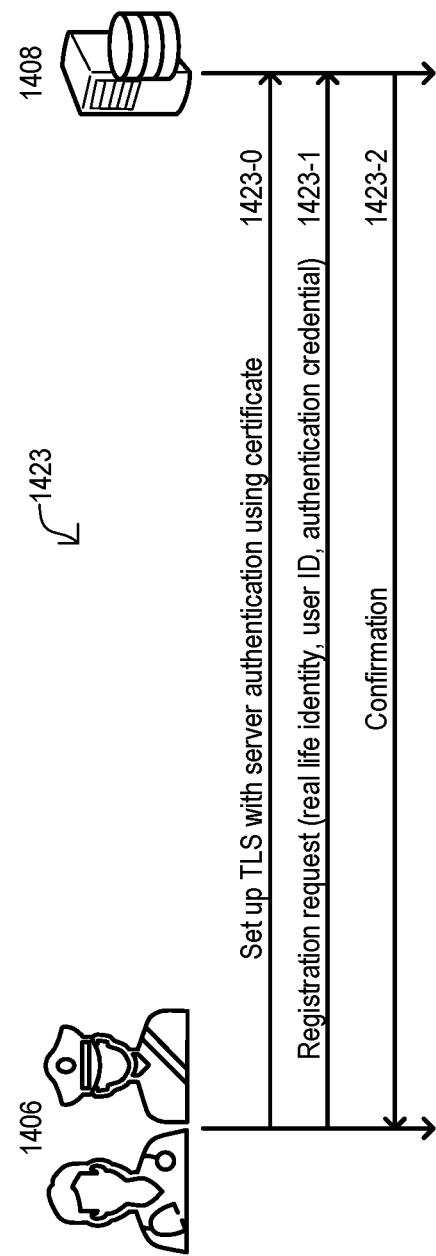
FIG. 14 is a communication diagram of an authority registration operation according to an embodiment.

FIG. 14 is a communication diagram showing an authority registration operation 1423 according to an embodiment. Operation 1423 show communications between an authority 1406 and a server system 1408. As described herein, an authority can be a special type of user. An authority 1406 can register to a server system 1408 with a real identity, such that the server system can verify and trust the authority. In the embodiment shown, a TLS connection can be created between the authority 1406 and the server system, with authority-to-server authentication being by certificate 1423-0. An authority can request registration with the server system, which can involve confirming real life identity, providing an authentication credential for the authority, and the authority can receive a user ID 1423-1. If the authority registration is successful, the server system 1408 can provide confirmation 1423-2.

Upon successful registration, the authority 1406 can have an account at the server system 1408. An authority account can include an authority user ID and some authentication credentials, which can be used to authenticate the authority to the server system. An authority can periodically requests tokens from the server system. Each token can include an expiration time. A server system does not track which token has been distributed to which authority.

Authorities can be doctors (for contagious disease tracking), police (for lost and found, witness discovery), or a server system operator (for targeted advertising), as but a few of many possible examples.

Figure 15:
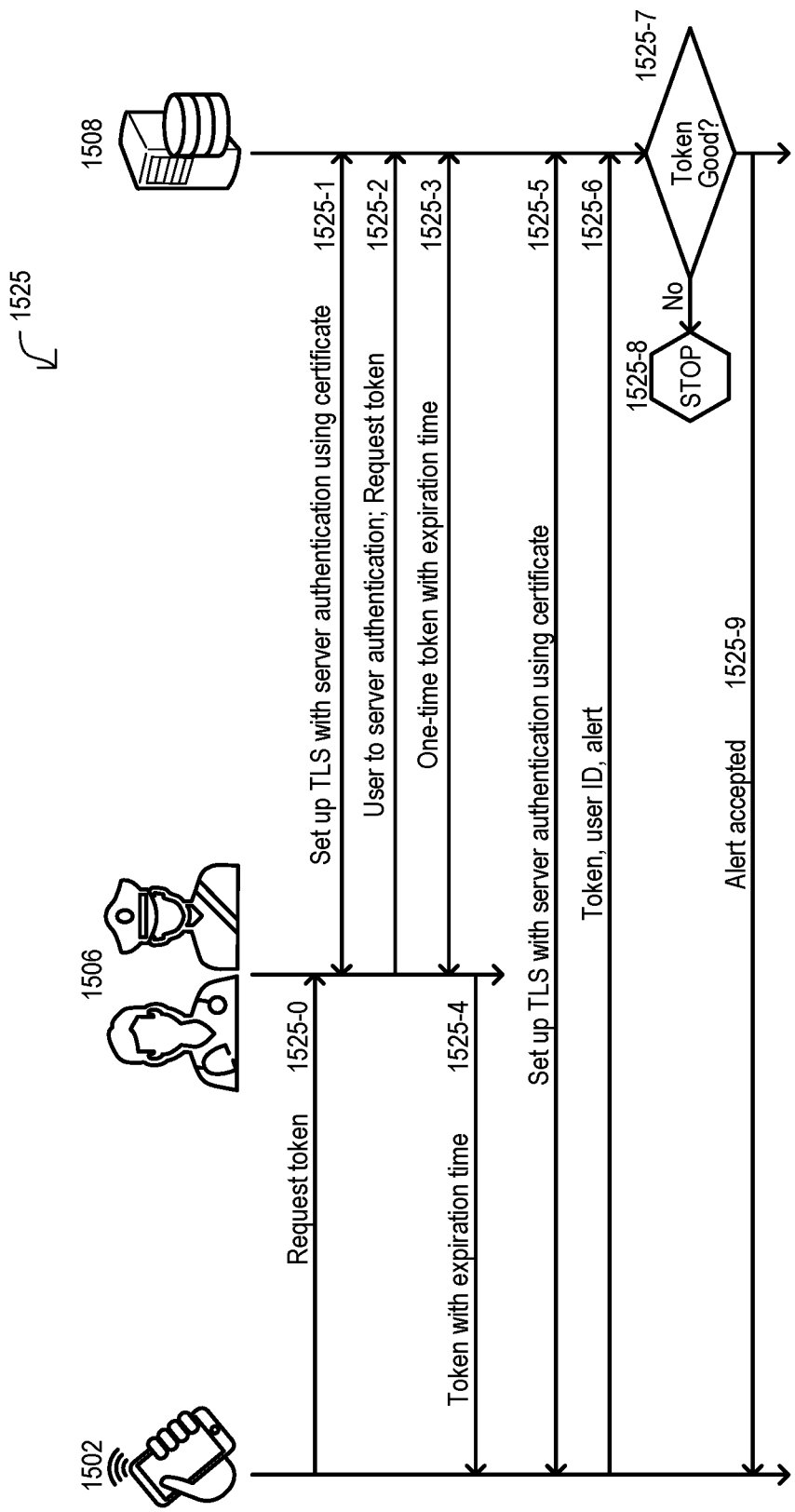
FIG. 15 is a communication diagram of an alert operation according to an embodiment.

FIG. 15 is a communication diagram showing alert operations 1525 according to an embodiment. Operations 1525 show communications between a user device 1502, an authority 1506, and a server system 1508. According to embodiments, a user can report an alert to a server system 1508 with a user device 1502. An alert can be for any suitable purpose, including but not limited to: the user is sick (for medical application) or the user lost something, or is asking for help, etc. (for social applications). An alert request must be validated by an authority 1506 before it can be accepted by the server system 1508. This can prevent hoaxes as noted herein. As understood from the description herein, an authority 1506 must be authenticated to the server system 1508. An authority 1506 can be the user's doctor (for medical application) or the police or other law enforcement, (for social applications), for example.

In an alert operation, a user device 1502 can request a token from an authority 1525-0. An authority 1506 can operate his/her device to get a token (along with an expiration time) from the server system. Such an action can include an authority establishing a TLS connection with the server system 1525-1. The authority can authenticate itself with the server system and request a token 1525-2. The authority 1506 can then receive a one-time token with expiration time 1525-3 from the server system 1508.

According to embodiments, a server system 1508 does not track which token has been distributed to which authority 1506. The authority 1506 does not know the token either, and can pass the token on to the user device 1525-4. Such an action can involve an authority 1506 using any secure communication method, such as email as but one of many possible examples. A token can be saved on the user device 1502, enabling the user to issue an alert to the server system 1508. It is noted that the authority does not know the user ID in the above process and does not know the token either.

To issue an alert, a user device 1502 can establish a TLS connection with the server system 1525-5. A user device 1502 can then send the token, user ID and alert to the server system 1525-6. It is noted that the server system 1508 does not know which authority gets which token. It only knows one of trustable authority has verified the user's alert and has issued the token to the user. Thus, when a server system receives an alert with a valid token, it signals the alert has be verified by an authority.

When a server system 1508 receives an alert with a token, it can determine if the token is good 1525-7. If the token is not good (e.g., expired or not a valid number), the alerting process can stop 1525-8. If the token is determined to be good, a server system 1508 can indicate to the user device that the alert has been accepted 1525-9.

After receiving and validating a token received with an alert, a server system can determine a starting time and a distance range based on information provided with the alert. The server system can then search appropriate tracking history files of the user device (based on user ID) and can mark user IDs for other devices that have been in close contact with the alerting device in the specified time period and distance range. Later, when a user device corresponding to a marked user ID uploads its close contact history file, an alert indication is sent back to the user device, thereby notifying the other user of the alert.

By encrypting beacon IDs with a server-generated encryption keys in the broadcast beacon data, the privacy of the beacon device can be preserved, as an observer cannot decrypt the beacon ID. The high degree of privacy protection represents a significant improvement over conventional solutions.

According to embodiments, the users of a system can be anonymous to the server system, so users are protected with strong privacy. Beacon data broadcast by a beacon device can have a beacon ID encrypted using a server-generated public key, so no observer can detect the beacon ID and associate it with the corresponding user at the location.

According to embodiments, an authority must validate a user's alert before the alert can be sent to the tracking server, to thereby prevent hoax alerts, while at the same time enabling users to remain anonymous to the server system.

Embodiments disclosed herein can include systems and methods of using WLAN and/or BLE devices to track close contact history of users, and send alert information to relevant users without revealing anyone's identity. Embodiments can include many applications in addition to tracking diseases, such as lost and found, witness discovery, targeted advertising, all with strong privacy protection to users.

In contagious disease tracking applications, users can include the general public. Authorities can include health care providers such as doctors or the like. An alert can be a warning to users that may have been in close contact with an infected user.

In lost and found applications, users can be the general public. Authorities can include personnel at a location, police, or security, for example. An alert can be a request for information regarding a lost item (e.g., if it was found by another user or ever in proximity of a user).

In witness discovery applications, users can be the general public. Authorities can be law enforcement. An alert can be a call for witnesses for all users in proximity of an incident site within a predetermined time window.

In anonymous targeted advertising applications, users can be the general public and merchants. A server system can have a database based on a "close contact" time with a beacon device installed at a merchandise spot. A server system can be operated by an advertisement entity who can serves as the authority. A merchant can send targeted advertisements as an "alert" to all users that stopped at the merchant sites for certain duration (which implies the users have interest to the merchandize).

Embodiments can provide reliable and credible tracking and alerting functions, based on close contact history between participating users. Relevant users can be notified by the alert information sent by a user via the server system.

According to embodiments, alerts can be credible as they are verified by an authority.

By including current time and optionally current location into an encrypted beacon data block along as well as an unencrypted data block, embodiments can advantageously prevent replay attacks and the injection of false beacon data.

According to embodiments, users have greater privacy protection than conventional approaches, as a person cannot be associated with transmissions at a location, which can occur with systems using RPIs.

Advantageously, a user's real identity is never known by the server system or by other users. While an authority can know a user's identity, the authority will not know a user's tracking history (i.e., accumulated beacon data).

Advantageously, a beacon ID included in broadcasted beacon data is encrypted (using a server-generated public key) along with broadcasting time and location. This can defeat replay attacks, as an encrypted time/location must match an unencrypted time/location. According to embodiments, only a server system can decrypt a beacon ID using the corresponding private key identified by the key ID. Thus, there is no chance for an observer to associate a user ID with a user's real identity, as can occur in conventional approaches.

According to embodiments, a beacon device can broadcast ever-changing, encrypted beacon data along with a randomized MAC address, which can be essentially impossible for any listening device to track or identify a user.

It should be appreciated that reference throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention.

Similarly, it should be appreciated that in the foregoing description of exemplary embodiments of the invention, various features of the invention are sometimes grouped together in a single embodiment, figure, or description thereof for the purpose of streamlining the disclosure aiding in the understanding of one or more of the various inventive aspects. This method of disclosure, however, is not to be interpreted as reflecting an intention that the claims require more features than are expressly recited in each claim. Rather, inventive aspects lie in less than all features of a single foregoing disclosed embodiment. Thus, the claims following the detailed description are hereby expressly incorporated into this detailed description, with each claim standing on its own as a separate embodiment of this invention.

What is claimed is:

1. A method, comprising:
by operation of a user device, receiving beacon data via a wireless signal, the beacon data including
unencrypted data that includes a key identification (ID) corresponding to a private key/public key pair, a time value, and a location value, and
encrypted data that includes at least a beacon ID, a beacon time value, and a beacon location value;
determining that at least the unencrypted time value is within a predetermined range of a current time value of the user device;
storing the beacon data in a user record with at least a user ID;
periodically uploading the user record to a tracking system; and
receiving a user key ID and public encryption key from the tracking system,
wirelessly transmitting user beacon data including
user unencrypted data that includes the user key ID, a user time value, and a user a location value, and user encrypted data generated by encrypting at least the user ID, the user time value, and the location value with the public encryption key; wherein the user beacon data is transmitted with a randomized network address to mask identification of the user device.

2. The method of claim 1, further including:
by operation of the user device, in response to receiving the beacon data, determining a distance to a source of the beacon data.

3. The method of claim 2, wherein:
receiving the beacon data includes receiving a packet compatible with a standard selected from the group of: at least one IEEE 802.11 wireless standard, and at least one Bluetooth standard, including a Bluetooth Low Energy (BLE) standard; and
determining the distance is selected from a fine time measurement operation and an angle of arrival measurement.

4. The method of claim 1, further including:
by operation of the user device, establishing an anonymous connection with the tracking system;
authenticating the tracking system; and
receiving at least the user ID from the tracking system.

5. The method of claim of 1, wherein:
wirelessly transmitting the user beacon data includes transmitting a packet selected from the group of: a beacon packet compatible with at least one IEEE 802.11 wireless standard and an advertisement packet compatible with at least one Bluetooth standard, including the BLE standard.

6. The method of claim 1, further including:
receiving a token from an authority;
transmitting the token with the user ID and an alert indication to the tracking system; wherein
the authority is an entity authenticated with the tracking system, and
the token expires after a predetermined amount of time.

7. A device, comprising:
a nonvolatile memory (NVM) configured to store at least a user identification (ID), a user public encryption key and corresponding key ID, and a user tracking record;
wireless circuits configured to receive beacon data according to at least one protocol, the beacon data including
unencrypted data that includes a key ID corresponding to a private key/public key pair, a time value, and a location value, and
encrypted data that includes at least a beacon ID, a beacon time value, and a beacon location value;
processing circuits configured to
determine that the unencrypted time value is within a predetermined range of a time for the device,
determine a user time value and user location value for the device,
add the received beacon data to the user tracking record with at least the user ID,
transmit the user tracking record to a tracking system via the wireless circuits,
generate encrypted user data by encrypting at least the user ID, the user time value, and the user location value with the public encryption key, generate a random network address, and
wirelessly transmit a beacon packet that includes the random network address, the encrypted user data and unencrypted user data via the wireless circuits, the unencrypted user data including the key ID, the user time value, and the user location value.

8. The device of claim 7, wherein:
the wireless circuits are configured to determine a distance to a source of the beacon data; and
the processing circuits are configured to include any determined distances to sources of beacon data in the user tracking record.

9. The device of claim 8, wherein:
the wireless circuits are selected from the group of: circuits compatible with at least one 802.11 wireless standard and at least one Bluetooth standard, including a Bluetooth Low Energy (BLE) standard; and
the wireless circuits determine the distance according to an operation selected from the group of: a fine time measurement operation and an angle of arrival measurement.

10. The device of claim 7, wherein:
the processing circuits are configured to wirelessly transmit the beacon packet according to a format selected from: a beacon packet compatible with an IEEE 802.11 wireless standard, and an advertisement packet compatible with the Bluetooth standard including the BLE standard.

11. The device of claim 7, wherein:
the processing circuits are further configured to
receive a token from an authority; and
transmit the token with the user ID and an alert indication to the tracking system; wherein
the authority is an entity authenticated with the tracking system, and
the token expires after a predetermined amount of time.

12. The device of claim 7, wherein:
the device comprises a personal electronic device; and
the wireless circuits comprise a combination integrated circuit device having communication circuits compatible with an IEEE 802.11 wireless standard, and a Bluetooth standard including the BLE standard.

13. A system, comprising:
at least one beacon device comprising
memory circuits configured to store a beacon identification (ID) value, a public encryption key, and a key ID corresponding to the public encryption key,
processing circuits configured to
determine a beacon time value and beacon location value,
generate encrypted data by encrypting at least the beacon ID value, the beacon time value, and the beacon location value with the public encryption key,
generate a random network address,
construct a beacon packet that includes the random network address, the encrypted data, and unencrypted data, the unencrypted data including the first key ID, the beacon time value, and the beacon location value, and
wireless circuits configured to wirelessly transmit the beacon packet according to at least one wireless protocol;
an antenna system coupled to the wireless circuits; and
a server system comprising server processing circuits and server memory circuits configured to
receive a user tracking record from at least one user device,
determine private keys from key IDs of the user tracking record, decrypt the encrypted values with corresponding private keys to generate at least decrypted time values, and merge entries of the user tracking record into a database in response to a comparison between decrypted time values to corresponding unencrypted time values, the user tracking record including a plurality of entries, each entry including at least a key ID, encrypted data, and an unencrypted beacon time value.

14. The system of claim 13, wherein:
the beacon packet is selected from: a beacon packet compatible with at least one IEEE 802.11 wireless standard and an advertising packet compatible with a Bluetooth standard including a Bluetooth low energy (BLE) standard.

15. The system of claim 13, wherein:
the at least one user device comprises
 a nonvolatile memory (NVM) configured to store at least
  a user ID, and
  the user tracking record;
 user wireless circuits configured to receive the beacon packet,
 user processing circuits configured to
  add the received beacon data to the user tracking record with at least the user ID if the unencrypted time value of the beacon packet is within a predetermined time of the user device, and
  transmit the user tracking record to the server system via the user wireless circuits.

16. The system of claim 13, wherein:
the server system is further configured to
 issue tokens with expiration times to authenticated authorities, and
 in response to receiving an alert with a valid token from the at least one user device, search the database for other user devices within a predetermined proximity to the user device within a predetermined time period.

17. The system of claim 13, further including:
at least one authority device configured to
 provide authentication to the server system,
 request and receive a token from the server system, and
 provide the token to the at least one user device.

* * * * *